United States Patent [19]
Williams

[11] Patent Number: 5,769,631
[45] Date of Patent: Jun. 23, 1998

[54] ORTHODONTIC DEVICE

[76] Inventor: Michael O. Williams, 58 Shoreline La., Gulfport, Miss. 39503

[21] Appl. No.: 688,110

[22] Filed: Jul. 29, 1996

Related U.S. Application Data

[63] Continuation-in-part of Ser. No. 526,686, Sep. 11, 1995, Pat. No. 5,645,422.

[51] Int. Cl.$^6$ .................................................. A61C 3/00
[52] U.S. Cl. ............................................................ 433/7
[58] Field of Search ..................................... 433/7, 18

[56] References Cited

U.S. PATENT DOCUMENTS

| | | | |
|---|---|---|---|
| 3,525,153 | 8/1970 | Gerber . | |
| 4,144,643 | 3/1979 | Krygier | 433/7 |
| 4,192,069 | 3/1980 | McAndrew | 433/21 |
| 4,347,054 | 8/1982 | Kraus et al. | 433/7 |
| 4,373,913 | 2/1983 | McAndrew | 433/7 |
| 4,384,851 | 5/1983 | McAndrews | 433/7 |
| 4,433,956 | 2/1984 | Witzig | 433/7 |
| 4,723,910 | 2/1988 | Keller | 433/7 |
| 4,773,853 | 9/1988 | Kussick | 433/6 |
| 5,064,370 | 11/1991 | Jones | 433/21 |
| 5,439,377 | 8/1995 | Milanovich | 433/7 |
| 5,505,616 | 4/1996 | Harwell | 433/21 |

*Primary Examiner*—Cary E. O'Connor
*Attorney, Agent, or Firm*—Paul M. Denk

[57] ABSTRACT

A orthodontic appliance having a midarch expander positioned between two forward orthodontic bands to effect intercanine arch length development and bilateral spring-loaded telescopic rod and tube assemblies for molar distalization and added arch length development in the mandibular or maxillary bicuspid area. In one embodiment of the invention the midarch expander is an jackscrew complex connecting a bilateral palate plate. Each side of the palate plate is attached to a canine and a molar with an orthodontic band. In another embodiment of the appliance, a molded palate plate is divided into four sections, two forward sections and two rear sections. Each forward section is attached to a canine tooth and each rear section is attached to a molar with an orthodontic band. The midarch expander is positioned between the two forward sections and the two rear sections are attached to their respective forward section by a spring-loaded telescopic rod and tube assembly.

14 Claims, 9 Drawing Sheets

ORTHODONTIC DEVICE

This application is a continuation-in-part of application Ser. No. 08/526,686, filed Sep. 11, 1995, now U.S. Pat. No. 5,645,422.

BACKGROUND OF THE INVENTION

This invention relates generally to orthodontic devices and, more specifically, to fixed mandibular arch and maxillary arch expanders.

Orthodontists treating children often need to gain space for unerupted mandibular incisors and increase intercanine distance for narrow archforms as well as distalize mandibular first molars so that a total increase of arch length is available in the lower dental arch from first molar to first molar. Furthermore, the orthodontist also may want to expand the palate correspondingly. Often there is a need for tooth extraction of permanent teeth due to crowding.

Mandibular and maxillary arch expanders are known to the art. However, such mandibular arch expanders are rather bulky in design, impede tongue mobility, are uncomfortable to wear and interfere with good oral hygiene. The devices must be substantial in design to resist torquing or leverage mechanics during chewing.

SUMMARY OF THE INVENTION

It is among the objects of the present invention to provide a mandibular arch expander to develop narrow forming mandibular or maxillary arches in growing children.

Another object of the present invention is to provide a mandibular or maxillary arch expander that prevents the need for extraction of permanent teeth due to crowding.

It is another object of the invention to provide a maxillary arch expander to expand the maxillary arch and palate in growing children.

Still another object of the present invention is to provide a mandibular or maxillary expander that can be preset at the desired tension prior to cementing the appliance into place.

Yet another object of the present invention is to provide a maxillary arch expander that can be easily adjusted after cementing into place.

Another object of the present invention is to provide a mandibular or maxillary expander that is lean in design, comfortable, and allows good oral hygiene.

Yet another object of the present invention is to provide a mandibular or maxillary arch expander that resists torquing or leverage mechanics against teeth during chewing.

A further object of the present invention is to provide a mandibular or maxillary arch expander that has no tissue supported components, does not impinge on gum tissue, and does not impede tongue mobility.

In accordance with the principles of the present invention, a mandibular or maxillary expander is provided having a midarch jackscrew complex for intercanine arch length development and bilateral spring-loaded telescopic rod and tube assemblies for molar distalization and added arch length development in the mandibular bicuspid areas. The appliance has four orthodontic bands, one at each corner, to attached to selected teeth to stabilize and secure the appliance in place. The appliance is fixed to the lower arch by first molar orthodontic bands and to the mandibular deciduous first molars with bicuspid bands. The midarch jackscrew complex is positioned between the front bands. The lateral development of the mandibular arch results from timely activation of the midarch screw. A spring-loaded telescopic rod and tube assembly extends between the front band and rear band on each side. The spring loaded telescopic rod and tube design allows the orthodontist to preset the desired tension by measuring spring compression. The spring-loaded telescopic rod and tube assemblies increase mesial distal arch length. There are occlusal rests on each tube to provide extra support to the telescopic rod and tube assembly.

In an alternative embodiment, the midarch jackscrew complex is replaced with a third spring-loaded telescopic rod and tube assembly which extends between the two front bands. The third spring-loaded telescopic rod and tube assembly has a preset spring tension.

A novel maxillary palatal expander employing a pair of spring loaded rods and tubes is also provided for use with the mandibular arch expander.

In other embodiments, the orthodontic bands are connected to various divided segments of a molded palate plate and the jackscrew or the spring-loaded telescopic rod and tube assemblies are positioned between the palate plate segments.

The mandibular appliance is used to gain space for unerupted mandibular incisors and increase intercanine distance for narrow archforms and to distalize mandibular first molars so that the total increase in arch length becomes available in the lower dental arch from first molar to first molar. The device is used in conjunction with the novel maxillary palatal expander when the maxilla is being developed and the mandibular arch needs to be expanded to maintain coordinated archforms. The appliance allows for simultaneous alignment of the mandibular incisors by allowing bonded brackets to be added and arch wires placed during the expansion.

The mandibular appliances are totally tooth supported and, due to the four band, four corner design, are stable and resists torquing.

BRIEF DESCRIPTION OF THE DRAWINGS

Corresponding reference figures indicate corresponding elements throughout the various drawings.

DESCRIPTION OF THE PREFERRED EMBODIMENT

Figure 1:
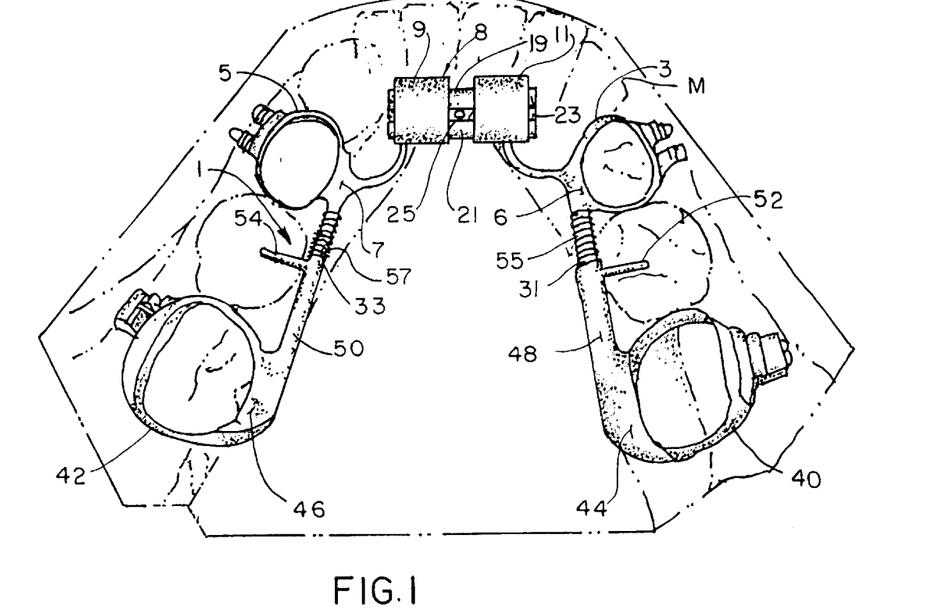
FIG. 1 is a perspective view of the orthodontic appliance of the present invention attached to a mold of the mandibular arch.
Figure 2:
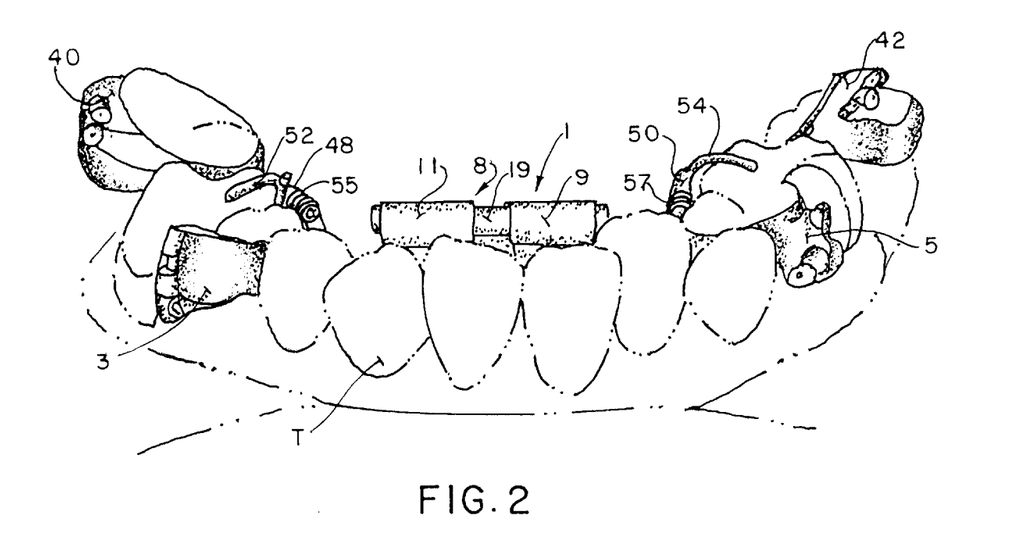
FIG. 2 is a front plan of the orthodontic appliance of the present invention attached to the mandibular arch.
Figure 3:
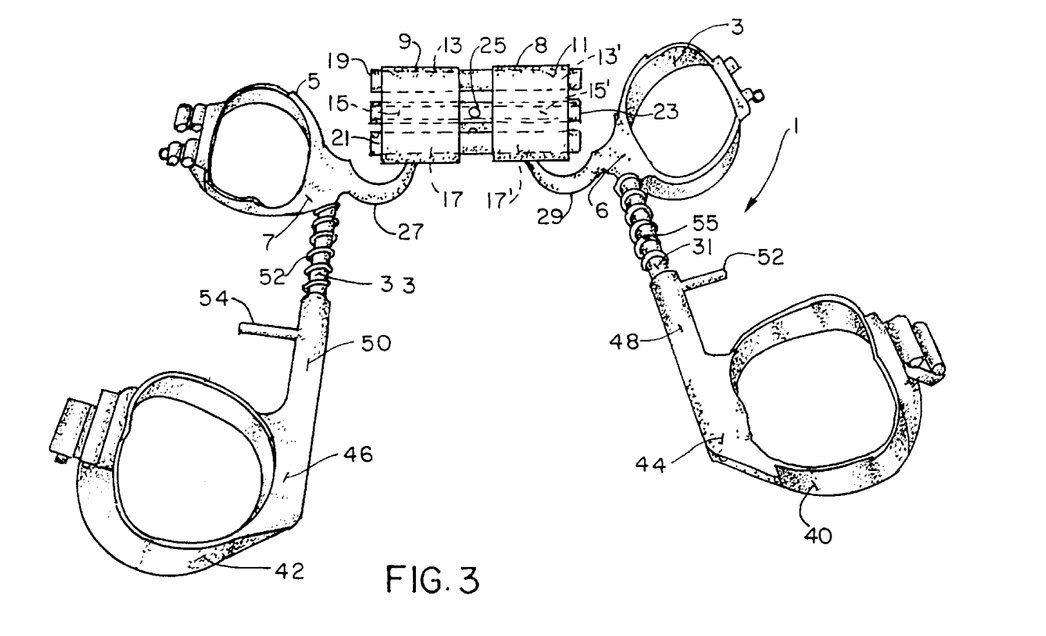
FIG. 3 is a bottom plan of the orthodontic appliance of the present invention.
Figure 4:
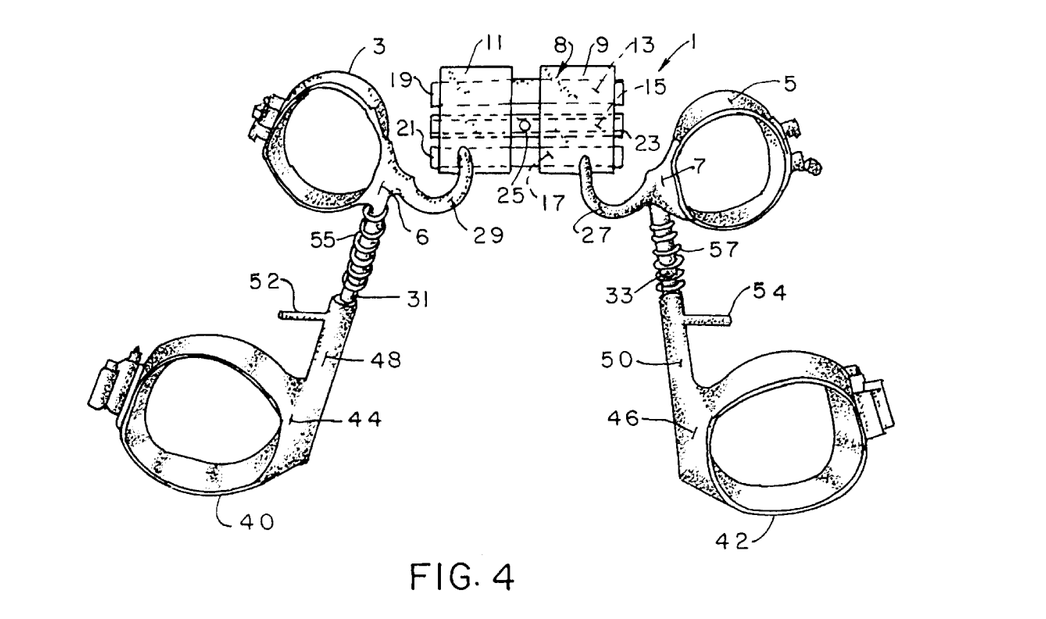
FIG. 4 is a top plan of the orthodontic appliance of the present invention.
Figure 5:
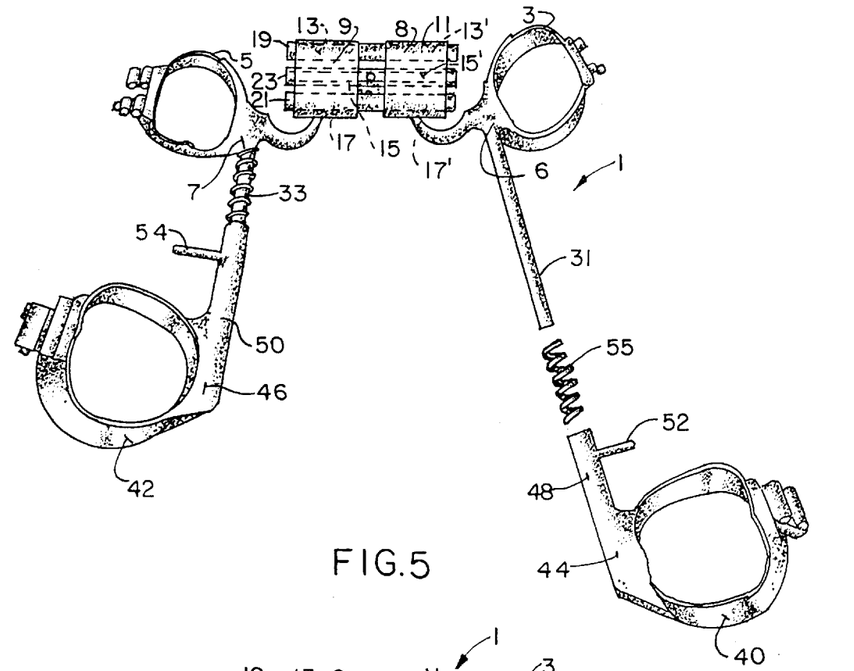
FIG. 5 is another bottom plan of the orthodontic appliance, the left spring-loaded tube assembly disassembled.
Figure 6:
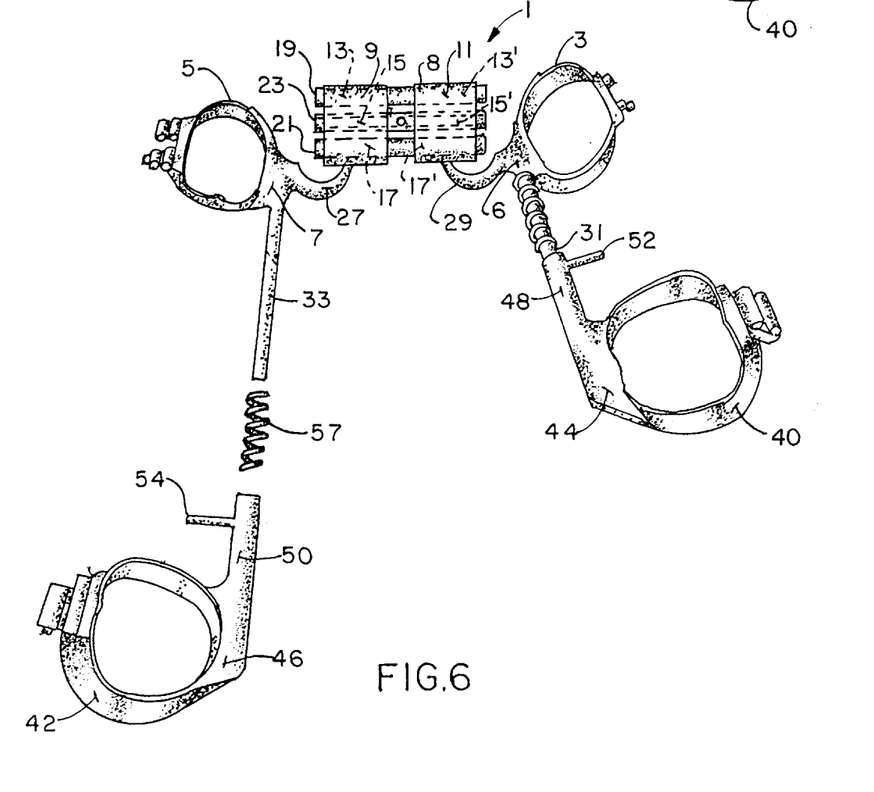
FIG. 6 is another bottom plan of the orthodontic appliance, the right spring-loaded tube assembly disassembled.

The mandibular expander appliance of the present invention is indicated generally in the drawings by reference numeral 1. Appliance 1 is shown, in FIG. 1, attached to a conventional dental mold M of the lower teeth. Appliance 1 is shown, in FIG. 2, attached to the lower teeth T of a human subject. Appliance 1 has a pair of space apart forward orthodontic bands 3 and 5. Bands 3 and 5 generally are conventional bicuspid bands and adapted to attach to the mandibular first primary molars. Band 3 has a boss 6 and band 5 has a boss 7, both positioned on the lingual side of the bands. The respective bosses are integrally formed on the respective bands to provide a substantial metallic body for the attachment of other elements to be described hereinafter.

The bands 3 and 5 are interconnected by an jackscrew complex 8. The jackscrew complex 8 has a first metal block 9 and a second metal block 11. First block has three bores 13,15 and 17 formed laterally therethrough and second block 11 has three bores 13', 15' and 17' formed laterally therethrough. Bores 13, 15 and are in substantial horizontal alignment with bores 13', 15' and 17'. The middle bores 15 and 15' are threaded. A first aligning pin 19 extends through bore 13 and a second aligning pin 21 extends through bore 17. The respective aligning pins are slightly undersized relative to the respective bores so that the blocks 9 and 11 can slide on the pins as will be described below.

A threaded screw 23 is threadedly engaged in bores 15 and 15'. It will be appreciated that threaded screw 23 has oppositely threaded ends. That is to say, the end of the screw that engages bore 15 is threaded opposite to the end that engages threaded bore 15'. There is at least one hole 25 formed through the middle of screw 23 between the oppositely threaded ends. Hole 25 accommodates the insertion of a small tool to turn screw 23. Therefore, when screw 23 is rotated in one direction, the blocks 9 and 11 are moved away from each other and when screw 23 is rotated in the opposite direction, the blocks 9 and 1 1 are drawn toward each other. The blocks 9 and 11 slide on the aligning pins 13 and 17 and the aligning pins serve to stabilize the jackscrew complex.

There is a first curved arm 27 extending between boss 6 and block 9 and a second curved arm 29 extending between boss 7 and block 11. The curved arms can be of any appropriate length and curvature to suitably engage the patient's teeth. The mold M is made following conventional procedures and the arms 27 and 29 are fabricated to be the appropriate length and curvature. The arms 27 and 29 then are soldered to the appropriate boss and to the jackscrew complex.

There is a first rod 31 attached to boss 6. Rod 3 can be a small hollow tube, to reduce weight, or can be a solid rod. A second rod 33 is attached to boss 7. A stated above, the exact position on the respective bosses where the rods are attached and the angle at which the rod extends from the boss depends upon the patient and the patient's needs. It will be appreciated that arm 27 and rod 31 can be one integral piece appropriately bent to form the arm and the rod or the arm and rod can be separate pieces. The same is true for arm 29 and rod 33.

Appliance 1 has a pair of spaced apart rear orthodontic bands, 40 and 42. Bands 40 and 42 generally are molar bands and, in use, are attached to the permanent first molars. Band 40 has an integral boss 44 and band 42 has an integral boss 46, with both bosses being positioned on the lingual side of the bands. There is a first hollow tube 48 attached to boss 44 and a second hollow tube 50 attached to boss 46. Each hollow tube has an internal bore sized to accommodate the sliding insertion of a rod, as will be explained in detail below, There is a first short wire 52 perpendicular to tube 48 and a second short wire 54 perpendicular to tube 50. The respective short wires extend buccally and serve as occlusal rests and are soldered on the respective tubs at a position corresponding to the lingual occlusal groove of the deciduous second molars bilaterally to provide extra support and stability to the tubes.

The forward pair of orthodontic bands are connected to the rear pair of orthodontic bands to promote molar distalization and added arch length development by a pair of spring-loaded telescopic rod and tube assemblies, as will now be described in detail. Rod 29 is slidingly engaged in tube 48. Rod 31 is slidingly engaged in tube 51. There is a first coil spring 55 positioned around rod 31 and fixed between boss 6 and the end of tube 48. Likewise, a second coil spring 57 is positioned around rod 33 and fixed between boss 7 and the end of tube 51. The coils springs are sized so they abut the ends of the tubes and do not slide over the tubes. The respective coil springs, therefore, urge the forward bands away from the tubes.

The respective coil springs have a preset tension. The preset tension of the spring is selected by the orthodontist to effect the appropriate mesial distal arch length development in the bicuspid area.

Figure 7:
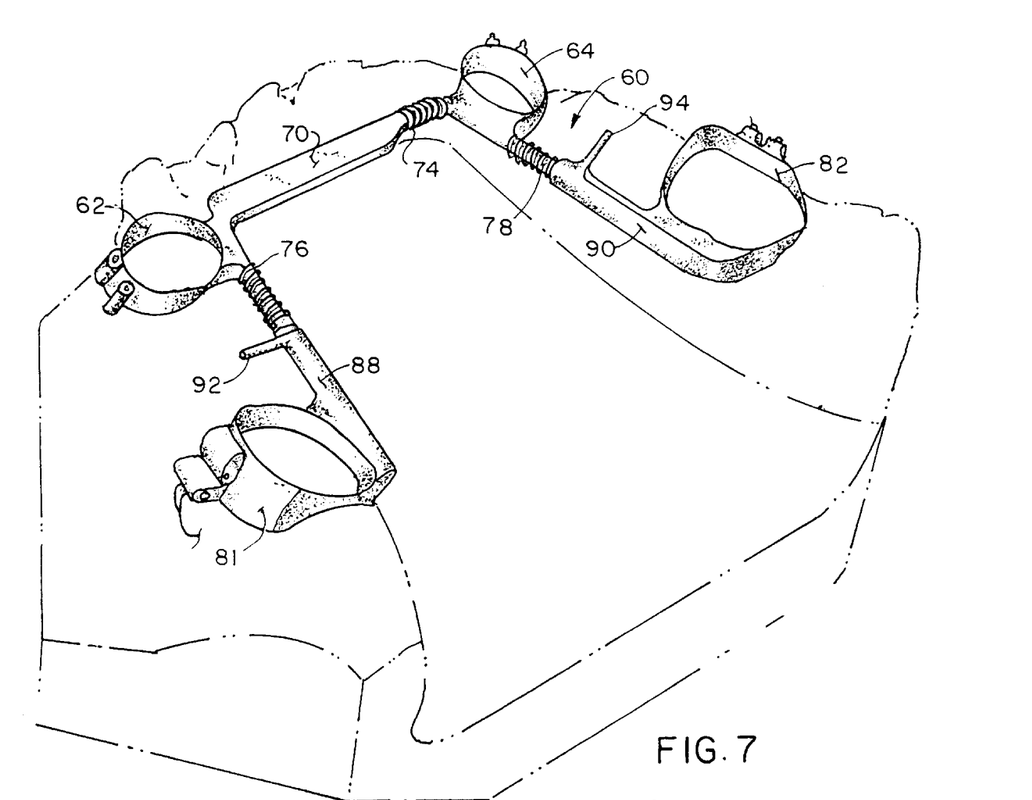
FIG. 7 is a perspective view of an alternative embodiment of the orthodontic appliance of the present invention attached to a dental mold.
Figure 8:
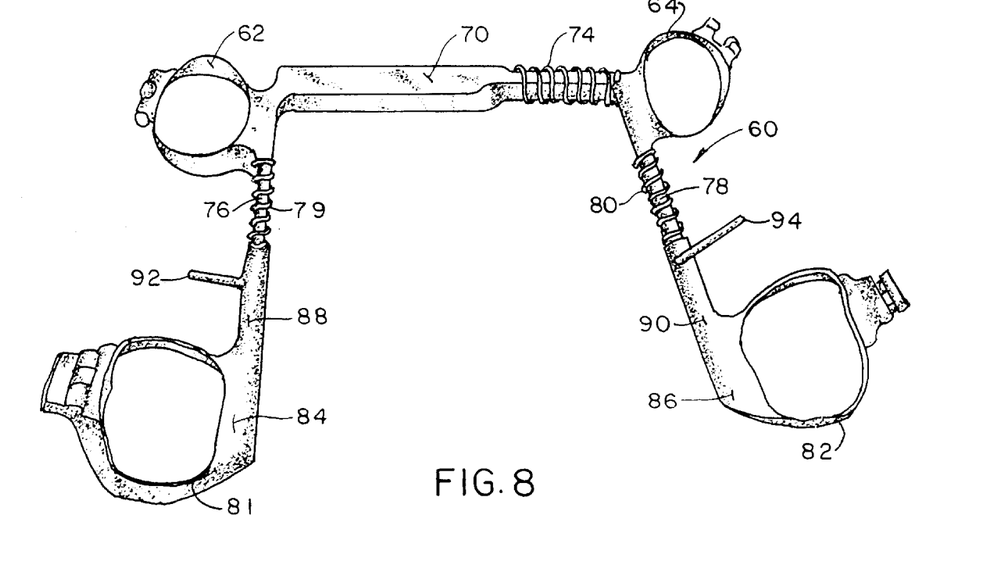
FIG. 8 is a bottom plan of the orthodontic appliance shown in FIG. 7.
Figure 9:
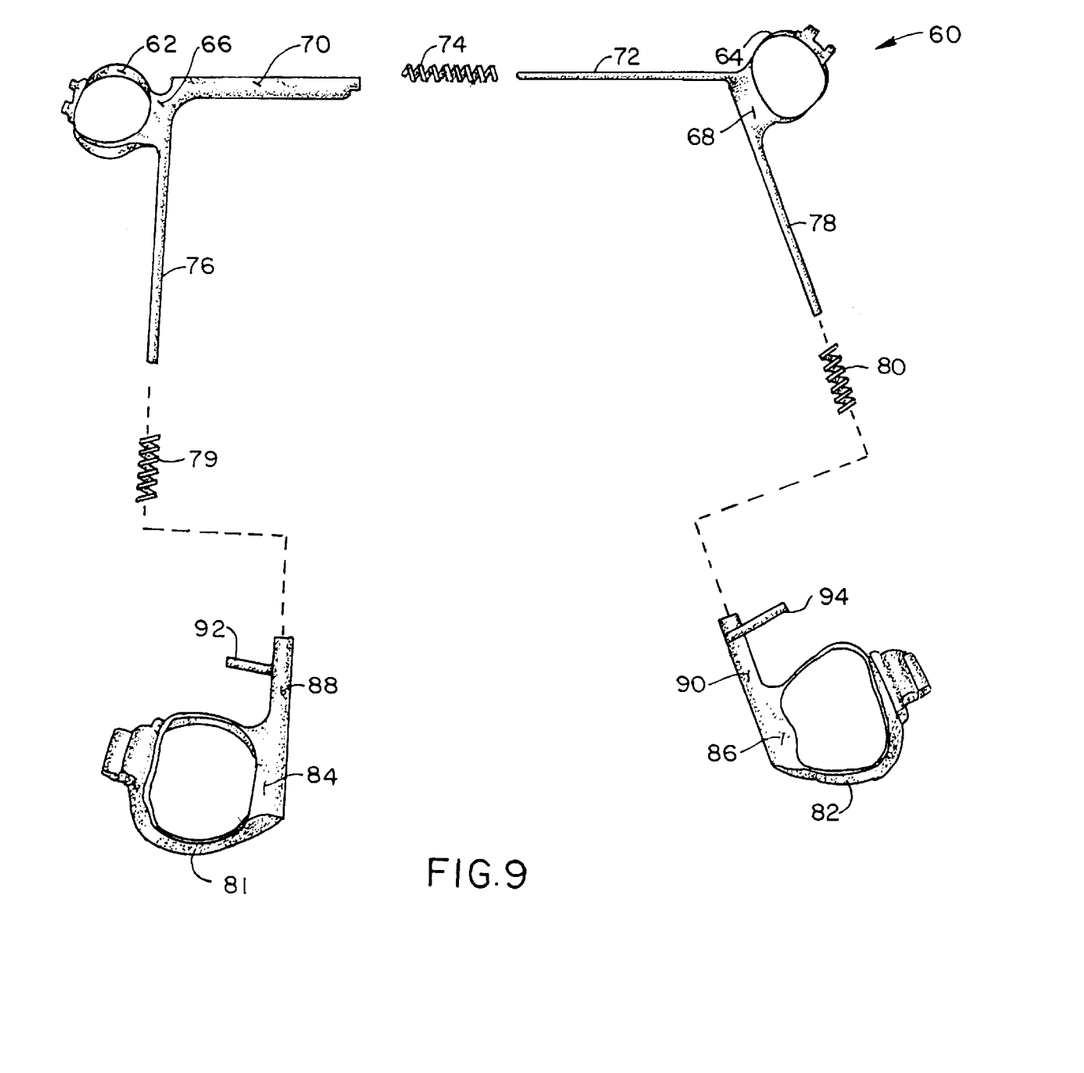
FIG. 9 is an exploded view thereof.

An alternative embodiment of the orthodontic appliance of the present invention is indicated in FIGS. 7–9 by reference numeral 60. Appliance 60 has a pair of spaced apart forward orthodontic bands 62 and 64. Band 62 and band 64 have bosses 66 and 68 integrally formed thereon. The bosses are positioned on the lingual side of the bands. There is a hollow tube 70 extending from boss 66 and a rod 72 extending from boss 68. The angles at which tube 70 and rod 72 extend from the respective bosses depends upon the shape of the patient's mouth. Rod 72 is slidingly engaged in tube 70. There is a coil spring 74 around rod 72 and fixed between boss 68 and the end of tube 70. Spring 74 is sized to engage the end of the tube and not slip over the tube. Therefore, spring 74 urges band 62 away from band 64. Spring 74 has a predetermined force to be delivered between the molars to widen the anterior canine width.

There is a first lateral rod 76 attached to boss 66 and second lateral rod 78 attached to boss 68. There is a first coil spring 79 around rod 76 and a second coil spring 81 around rod 78, abutting the respective bosses. The respective coil springs have a preset tension, as determined by the orthodontist to effect appropriate mesial distal arch length development.

It will be appreciated that rod 72 and rod 78 can be an integral L-shaped wire, appropriately bent and soldered to boss 68. The angles at which the respective lateral rods extend away from the respective bosses is dependent upon the corrective needs of the patient.

Appliance 60 has a pair of spaced apart rear orthodontic bands 81 and 82. Bands 81 and 82 have integrally bosses 84 and 86 respectively. There is a first hollow tube 88 attached to boss 84 and a second hollow tube 90 attached to boss 86. Each hollow tube has an internal bore sized to accommodate the sliding insertion of a rod, as previously explained. The hollow tubes are sized to allow the coil springs to abut the ends of the tubes without sliding over the tube, as previously described.

There is a first short wire 92 perpendicular to tube 88 and a second short wire perpendicular to tube 90. The respective short wires serve as occlusal rests and are soldered on the respective tubes at a position corresponding to the lingual occlusal groove of the deciduous second molars bilaterally to provide extra support and stability to the tubes.

The forward pair of orthodontic bands are connected to the rear pair of orthodontic bands in the same manner as previously described in reference to appliance 1.

Figure 10:
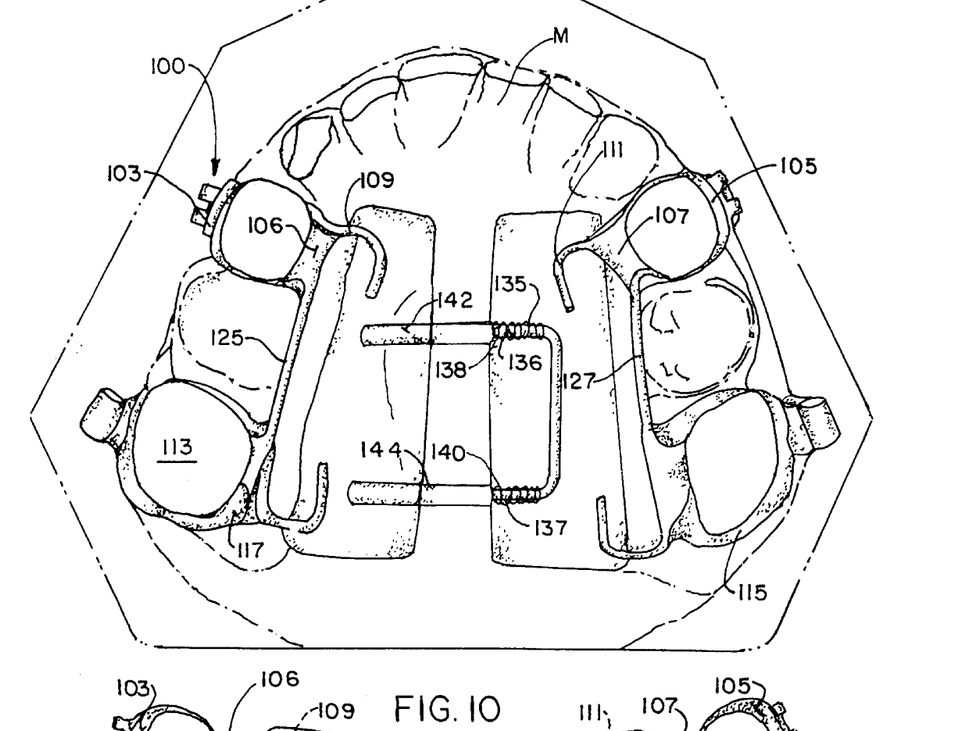
FIG. 10 is a bottom plan of an maxillary palatal expander of the present invention shown attached to a mold of the maxillary arch to demonstrate environment.
Figure 11:
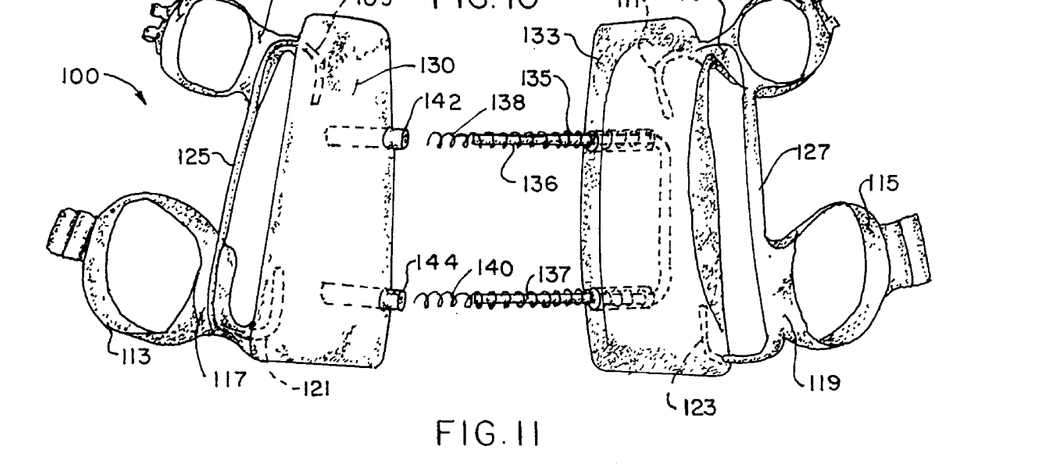
FIG. 11 is another bottom plan of the maxillary palatal expander, disassembled.

The maxillary palatal expander of the present invention is indicated generally by reference numeral 100 in FIGS. 10 and 11. Expander 100 is shown, in FIG. 10, attached to a conventional dental mold M of the upper teeth. Appliance 100 has a pair of spaced apart forward orthodontic bands 103 and 105. Bands 103 and 105 can be conventional bicuspid bands adapted to attach to the maxillary molars. Band 103 has a boss 106 and band 105 has a boss 107 both positioned on the lingual side of the bands. The respective bosses are integrally formed on the respective bands. There is an integral curved member or hook 109 on boss 106 and an integral curved member or hook 111 on boss 107.

Appliance 100 has a pair of spaced apart rear orthodontic bands 1 13 and 1 15. Band 1 13 has an integral boss 1 17 and band 1 15 has an integral boss 119, both on the lingual side of the respective bands. Boss 117 has an integral curved member or hook 121 and boss 119 has an integral curved member or hook 123.

The forward orthodontic bands are connected to the rear orthodontic bands as follows: a first rod 125 extends between boss 106 and boss 117. A second rod 127 extends between boss 107 and boss 119. Furthermore. Hooks 109 and 121 are embedded in a plastic plate 130. Hook 111 and 123 are embedded in a plastic plate 132.

The respective plastic plates are molded to fit the patient's palate. Each plate, with the associated forward and rearward bands, comprises half of the appliance. The halves of the appliance is biased away from each other to widen the maxillary arch. There is a substantially U-shaped rod 135 imbedded in plate 130. Legs 136 and 137 of rod 135 extend out from, and at substantially right angles to, the plastic plate. There are coil springs 138 and 140 around legs 136 and 137 respectively. There is a first short tube 142 and a second short tube 144 embedded in plate 132. The tubes extend out of the palate plate at substantially right angles to the palate plate. The tubes 142 and 144 are on complementary alignment with the legs 136 and 137. The tubes 142 and 144 are slightly oversized so that the legs 136 and 137 can slide into the tubes. The springs 138 and 140 abut the ends of the tubes and exert tension force to urge the halves of the appliance apart. The appropriate tension can be exerted by selecting springs with the appropriate tension.

Figure 12:
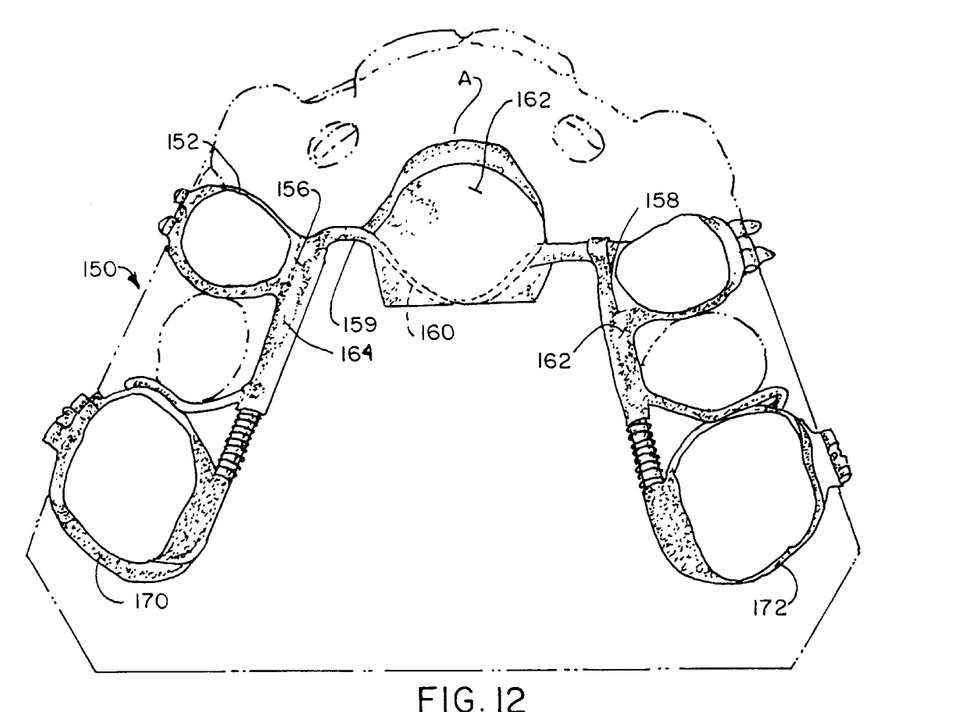
FIG. 12 is a perspective view of another embodiment of an orthodontic appliance of the present invention attached to a mold of the maxillary arch.
Figure 13:
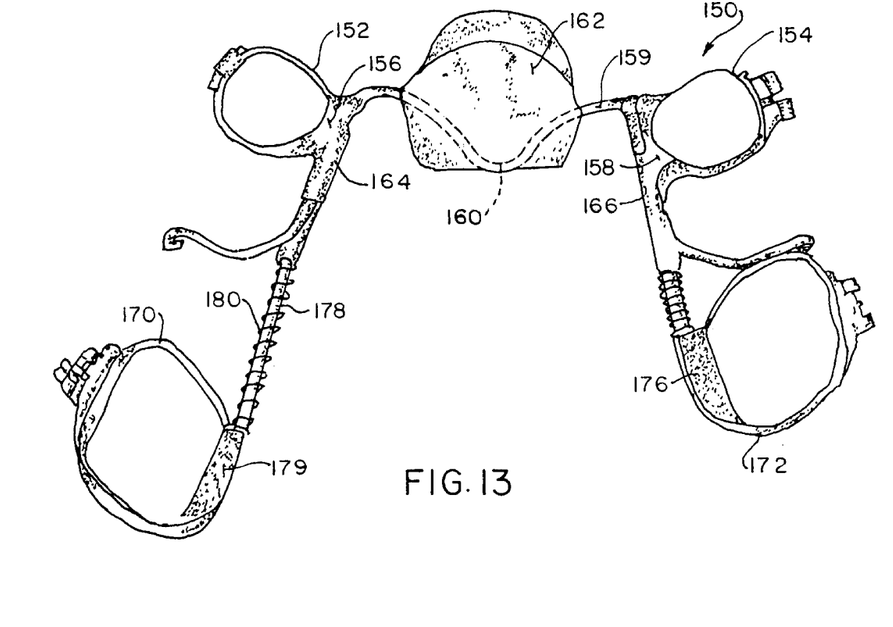
FIG. 13 is another perspective view of the orthodontic appliance of FIG. 12.

Another embodiment of the orthodontic appliance of the resent invention is indicated generally by reference numeral 150 in FIGS. 12 and 13. Appliance 150 includes a pair of spaced apart forward orthodontic bands 152 and 154. Bands 152 and 154 include bosses 156, 158 integrally formed thereon. The bosses are positioned on the lingual side of the bands. There is a connecting wire 159 extending between the bosses connecting band 152 and band 154. It will be appreciate that the length of wire 159 is dictated by the width of the mandibular arch A. Wire 159 includes a bend or bow 160. Wire 159 can be embedded in a piece of plastic 162 or acrylic nance button other material that fits in arch A for anchorage. A hollow tube 164 extending from boss 156 and a hollow tube 166 extending from boss 158. The angles at which the respective tubes extend from the respective bosses depends upon the morphology of arch A.

Apparatus 150 also includes a pair of spaced apart rear orthodontic bands 170 and 172. Band 170 includes an integral boss 179 and band 172 includes boss 176. A rod 178 is integrally connected to boss 179 and slidingly engages in tube 164. There is a coil spring 180 around rod 178 and fixed between boss 179 and the end of tube 164. Spring 180 is sized to abut the end of tube 164 and not slip over the tube and is constructed from nickel titanium to deliver low continuous force. Thus, spring 180 urges band 170 away from band 152. Spring 180 has a predetermined force to be delivered between the teeth to distalize maxillary molars.

Figure 14:
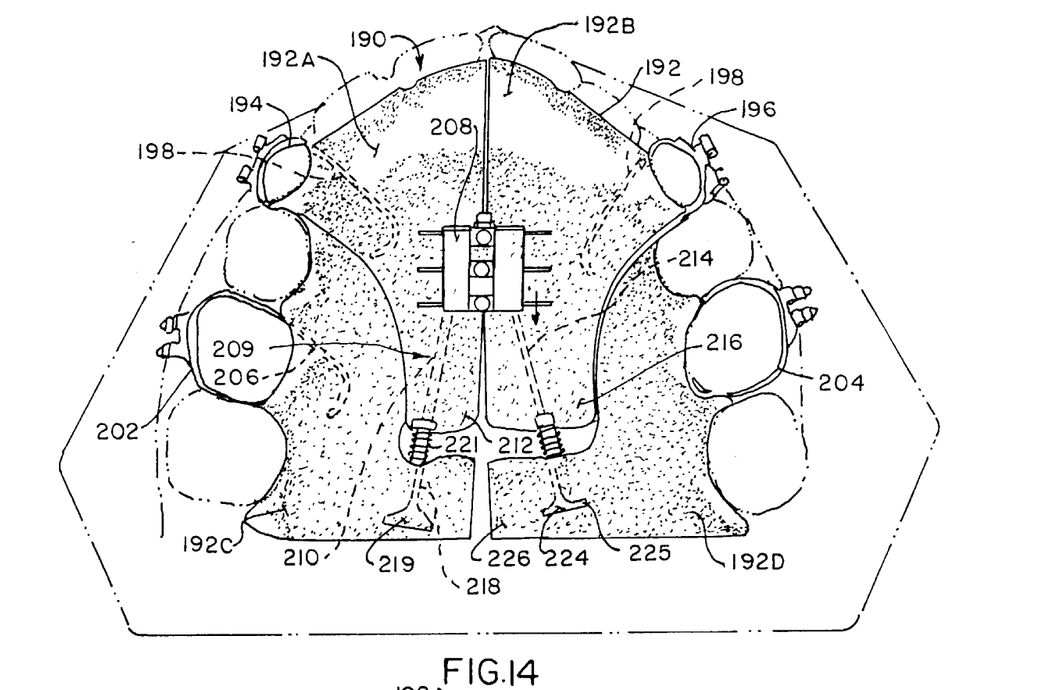
FIG. 14 is a perspective view of another embodiment of an orthodontic appliance of the present invention attached to a mold of the maxillary arch.
Figure 15:
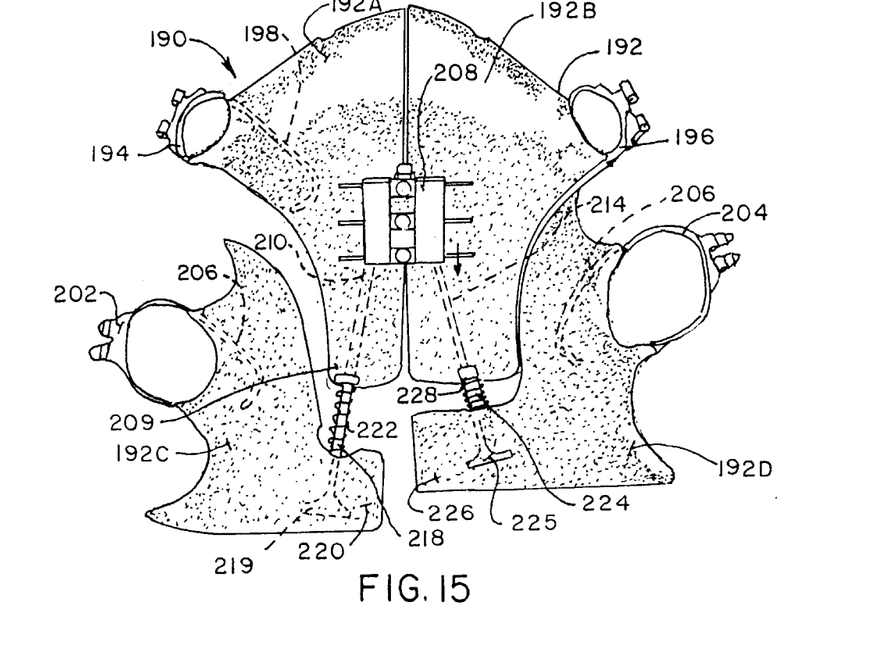
FIG. 15 is another perspective view of the orthodontic appliance of FIG. 14.

FIGS. 14 and 15 illustrate another embodiment of an orthodontic appliance of the present invention indicated generally by reference numeral 190. Appliance 190 includes a molded palate plate indicated generally by reference numeral 192. Palate plate 192 is molded from an appropriate resin material as assumes the shape of and conforms to the patient's hard palate. Palate plate 192 is divided into four quadrants or sections 192A, 192B, 192C and 192D. It will be appreciated that the palate plate 192 is molded and constructed as one piece and then divided into the four sections 192A, 192B, 192C and 192D by appropriate means. Section 192A includes an orthodontic band 194 attachable to an incisor or canine or the like. Likewise, section 192B includes a similar orthodontic band 196. The orthodontic bands 192A and 192B each include an integral wire or hook 198 which is molded into the palate plate to secure the orthodontic band in place. Correspondingly, sections 192C and 192D include orthodontic bands 202 and 204, respectively. Orthodontic bands 202, 204 include wires or hooks 206 which are molded into the palate plate to secure the orthodontic band in place. Orthodontic bands 202, 204 are positioned to attach to molars.

Section 192A is connected to section 192B by an jackscrew complex 208, which functions like the previously described jackscrew complexes. Further, section 192A and 192C are connected by a telescopic rod and tube assembly 209 as can also be seen at 221. Telescopic rod and tube assembly 209 includes a tube 210 molded in a distal tail 212 of section 192A. Likewise, section 192B is connected to section 192D with telescopic rod and tube assembly 213. Telescopic rod and tube assembly 213 includes a tube 214 molded in a distal tail 216 of section 192B. Section 192C has a rod 218 molded into a lateral section 220. Rod 218 has a transverse section 219 to anchor it in place within the palate plate section and to prevent it from piercing the section under pressure. There is a coil spring 222, preferably constructed from nickel titanium having a predetermined tension, around rod 218. Rod 218 seats in tube 210. Section 192D likewise has a rod 224 molded into a lateral section 226. Rod 224 has a transverse section 225 to anchor it in place within the palate plate section and to prevent it from piercing the palate section under pressure. There is a coil spring 228, having a predetermined tension around rod 224. Rod 224 seats upon tube 214.

Appliance 190 can exert both arch widening and arch lengthening forces. Jackscrew complex 208 can be manipulated to exert an appropriate force on plate sections 192 and 192A to urge them apart and thus effect widening of the arch. Further, telescopic rod and tube assembly 209 can exert a lengthening force between sections 192A and 192C while telescopic rod and tube assembly 213 can exert an appropriate lengthening force between sections 192B and 192D.

Figure 16:
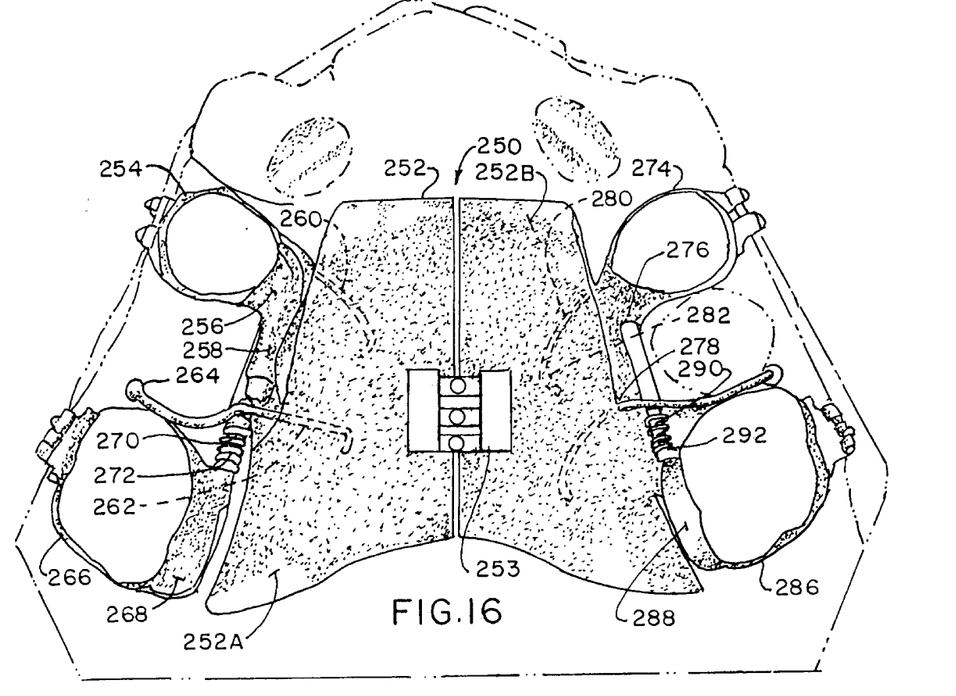
FIG. 16 is a perspective view of another embodiment of an orthodontic appliance of the present invention attached to a mold of the maxillary arch.
Figure 17:
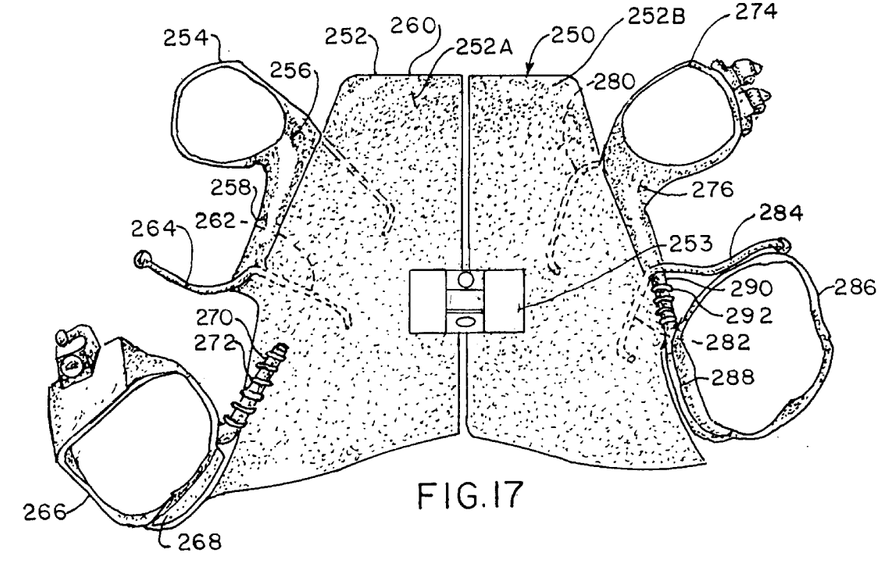
FIG. 17 is another perspective view of the orthodontic appliance of FIG. 16.

Another alternative embodiment of the orthodontic appliance of the present invention is indicated generally by reference numeral 250 in FIGS. 16 and 17. Appliance 250 includes a molded palate plate 252. Palate plate is appropriately molded and then divided into two halves 252A and 252B. The two halves are movably joined by an jackscrew complex 253. It will be appreciated that the jackscrew complex 253 can be replaced with a telescopic rod and tube assembly without departing from the scope of the invention. The first half 252A includes a first forward orthodontic band 254 or attachment to an incisor or canine tooth. Orthodontic band 254 includes a boss 256 integrally formed thereon. There is a hollow tube 258 extending from boss 256. There is a first wire hook 260 adjacent boss 256 and a second wire hook 262 adjacent the hollow tube which are molded into the palate plate to secure the orthodontic band and tube to the palate plate. An occlusal rest 264 is integrally formed at the distal end of tube 258 on the buccal side.

Appliance 250 includes a first rear orthodontic band 266 for attachment to a rear molar. Rear orthodontic band 266 includes an integral boss 268. A rod 270 is integrally attached to boss 268 and disposed to slidingly engage hollow tube 258. There is a coil spring 272 having a predetermined tension around rod 270.

The second half 252B includes a first forward orthodontic band 274 for attachment to an incisor or canine tooth. Orthodontic band 274 includes a boss 276 integrally formed thereon. There is a hollow tube 278 extending from boss 276. There is a first wire hook 280 adjacent boss 276 and a second wire hook 282 adjacent the hollow tube which are molded into the palate plate to secure the orthodontic band and tube to the palate plate. An occlusal rest 284 is integrally formed at the distal end of tube 268 on the buccal side.

Appliance 250 also includes a second rear orthodontic band 286 for attachment to a molar. Rear orthodontic band 286 includes an integral boss 288. A rod 290 is integrally attached to boss 288 and disposed to slidingly engage hollow tube 278. There is a coil spring 292 having a predetermined tension around rod 290.

Appliance 250 can be used to both widen and lengthened the maxillary arch. Or example, when appliance 250 is attached to the patient's teeth, jackscrew complex 258 can be manipulated to urge apart plate halves 252A and 258B, thus widening the arch. Further, the coil springs 272, 292 function to urge the respective rear orthodontic bands away from the corresponding front orthodontic bands and thereby exert lengthening forces on the maxillary arch.

It will be appreciated that various changes and modifications may be made in the orthodontic appliance of the present invention without departing from the scope of the appended claims. Therefore, the foregoing description and accompanying drawings are intended to be illustrative only and should not be construed in a limiting sense.

What is claimed:

1. A fixed maxillary arch expander comprising;
   a first forward orthodontic band and a second forward orthodontic band;
   an expansion means between said first and second orthodontic band;
   a first rear orthodontic band;
   a first spring-loaded telescopic rod and tube assembly connecting said first forward orthodontic band to said first rear orthodontic band a second rear orthodontic band;
   a second spring-loaded telescopic rod and tube assembly connecting said second forward orthodontic band to said second rear orthodontic band;
   wherein said expansion means between said first and second forward orthodontic bands effects lateral maxillary arch expansion and said first and second spring loaded telescopic rod and tube assemblies effect distal arch length expansion.

2. The fixed maxillary arch expander of claim 1 further comprising a first occlusal rest on said first telescopic rod and tube assembly and a second occlusal rest on said second telescopic rod and tube assembly.

3. An orthodontic appliance for expanding the maxillary arch comprising:
   a first forward orthodontic band;
   a first rear orthodontic band;
   a first spring-loaded telescopic rod and tube assembly connecting said first forward orthodontic band to said first rear orthodontic band;
   a first palate plate connected to said first forward orthodontic band;
   a second forward orthodontic band;
   a second rear orthodontic band;
   a second spring-loaded telescopic rod and tube assembly between said second forward orthodontic band and said second rear orthodontic band;
   a second palate plate connected to said second forward orthodontic band; and
   an jackscrew complex between said first second palate plate.

4. The orthodontic appliance of claim 3 wherein said first palate plate extends a length between said first forward orthodontic band and said first rear orthodontic band and said second palate plate extends a length between said second forward orthodontic band and said second rear orthodontic band.

5. The orthodontic appliance of claim 4 wherein a linear relationship between the first and second palate plates can be adjusted by the jackscrew complex.

6. The orthodontic appliance of claim 3 and including further expansion means provided between the first palate plate and said second palate plate, said expansion means including spring means for continuously urging said palate plates into separation.

7. An orthodontic appliance comprising:
   a first forward palate plate having a first forward orthodontic band thereon;
   a second forward palate plate having a second forward orthodontic band thereon;
   an jackscrew assembly between said first and second forward palate plats;
   a first rear palate plate having a first rear orthodontic band thereon;
   a second rear palate plate having a second rear orthodontic band thereon
   a first spring-loaded telescopic rod and tube assembly connecting said first forward palate plate to said first rear palate plate; and a second spring-loaded telescopic rod and tube assembly connecting said second forward palate plate to said second rear palate plate.

8. The orthodontic appliance of claim 7 wherein the said palate plates are formed as one molded contiguous palate plate and then separated into the respective forward and rear palate plates.

9. An orthodontic appliance for expanding the maxillary arch comprising:
    a first forward orthodontic band;
    a second forward orthodontic band;
    a spring-loaded rod and tube assembly between said first and second orthodontic bands;
    a first rear orthodontic band;
    a spring-loaded rod and tube assembly connecting said first forward orthodontic band and said first rear orthodontic band;
    a second rear orthodontic band; and
    a spring-loaded rod and tube assembly connecting said second forward orthodontic band and said second rear orthodontic band.

10. The orthodontic appliance of claim 9 wherein each said spring-loaded rod and tube assembly contains a coil spring of an appropriate pre-set tension.

11. The orthodontic appliance of claim 9 having a first occlusal rest on said first rod and tube assembly and a second occlusal rest on said second rod and tube assembly.

12. An orthodontic appliance for expanding the maxillary arch comprising:
    a first forward orthodontic band;
    a second forward orthodontic band, rod means connecting between said first and second orthodontic bands;
    a first rear orthodontic band;
    a spring-loaded rod and tube assembly connecting said first forward orthodontic band and said first rear orthodontic band;
    a second rear orthodontic band; and
    a spring-loaded rod and tube assembly connecting said second forward orthodontic band and said second rear orthodontic band.

13. The orthodontic appliance of claim 12 and including palate plate means connecting intermediate said first and second orthodontic bands.

14. An orthodontic appliance for conformed fitting within a patient's mouth and for expanding the maxillar arch comprising:
    a first forward orthodontic band, a first rear orthodontic band, a first palate plate connecting said first forward and first rear orthodontic bands together; a second forward orthodontic band, a second rear orthodontic band, a second palate plate connecting said second forward orthodontic band and said second rear orthodontic bands together;
    said first and second palate plates being sized to substantially fit in proximity with a major portion of a patient's palate when the orthodontic appliance is installed within a patient's mouth; and
    a jack screw complex between said first palate plate and said second palate plate to urge said plates into separation for providing arch expansion.

* * * * *

UNITED STATES PATENT AND TRADEMARK OFFICE
CERTIFICATE OF CORRECTION

PATENT NO. : 5,769,631
DATED : June 23, 1998
INVENTOR(S) : Michael O. Williams

It is certified that error appears in the above-indentified patent and that said Letters Patent is hereby corrected as shown below:

Claim 3, lines 38 and 39 should read:
---a jackscrew complex between said first palate plate and said second palate plate.---

Claim 7, line 59, "an" should read ---a---.

Claim 14, line 15, replace "maxillar" with ---maxillary---.

Signed and Sealed this

Twentieth Day of October, 1998

Attest:

BRUCE LEHMAN

Attesting Officer

Commissioner of Patents and Trademarks